United States Patent
Song et al.

(10) Patent No.: US 11,759,343 B2
(45) Date of Patent: Sep. 19, 2023

(54) DISTAL END STRUCTURE OF SHEATH FOR DELIVERING INTERVENTIONAL INSTRUMENT AND SHEATH

(71) Applicant: VENUS MEDTECH (HANGZHOU), INC., Zhejiang (CN)

(72) Inventors: Wei Song, Hangzhou (CN); Jianan Wang, Hangzhou (CN); Yu Zhang, Hangzhou (CN); Xiangyu Shao, Hangzhou (CN)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 92 days.

(21) Appl. No.: 17/237,349

(22) Filed: Apr. 22, 2021

(65) Prior Publication Data
US 2022/0000645 A1    Jan. 6, 2022

(30) Foreign Application Priority Data
Jul. 6, 2020  (CN) .......................... 202010639551.8

(51) Int. Cl.
*A61F 2/962* (2013.01)
*A61F 2/24* (2006.01)

(52) U.S. Cl.
CPC ............ *A61F 2/962* (2013.01); *A61F 2/2436* (2013.01); *A61F 2/2439* (2013.01); *A61F 2210/0014* (2013.01); *A61F 2210/0076* (2013.01)

(58) Field of Classification Search
CPC .............. A61F 2/962; A61F 2210/0014; A61F 2210/0076; A61F 2/2436; A61F 2/2439
See application file for complete search history.

(56) References Cited

U.S. PATENT DOCUMENTS

| | | | |
|---|---|---|---|
| 6,214,036 B1 | 4/2001 | Letendre et al. | |
| 2001/0034549 A1* | 10/2001 | Bartholf | A61F 2/966 623/1.12 |
| 2007/0112355 A1 | 5/2007 | Salahieh et al. | |
| 2011/0098804 A1 | 4/2011 | Yeung et al. | |
| 2014/0012368 A1 | 1/2014 | Sugimoto et al. | |
| 2016/0220370 A1 | 8/2016 | Savage et al. | |

(Continued)

OTHER PUBLICATIONS

Office Action dated Feb. 28, 2023 for related U.S. Appl. No. 17/237,344.

*Primary Examiner* — Jing Rui Ou
(74) *Attorney, Agent, or Firm* — Raymond Sun

(57) ABSTRACT

A distal end structure of a sheath for delivering an interventional instrument includes a tubular body section which has opposite distal and proximal sides. A plurality of elastic expansion pieces is arranged circumferentially at the distal side of the body section at intervals. Each expansion piece assumes a converged configuration extending in an axial direction of the body section and a flared configuration away from each other. A connecting strip is provided between two adjacent expansion pieces, and two ends of the connecting strip are respectively connected to expansion pieces at respective sides at connection positions adjacent to distal ends of the expansion pieces. In the converged configuration of each expansion piece, a middle portion of the connecting strip is folded and received in a region between two adjacent expansion pieces; and in the flared configuration of each expansion piece, the middle portion of the connecting strip is unfolded.

19 Claims, 12 Drawing Sheets

(56) References Cited

U.S. PATENT DOCUMENTS

| | | |
|---|---|---|
| 2016/0317301 A1 | 11/2016 | Quadri et al. |
| 2017/0035567 A1* | 2/2017 | Duffy ................ A61M 25/0052 |
| 2017/0056171 A1* | 3/2017 | Cooper ............ A61M 25/0051 |
| 2017/0258584 A1* | 9/2017 | Chang .................... A61F 2/243 |
| 2019/0008639 A1 | 1/2019 | Landon et al. |
| 2020/0397575 A1 | 12/2020 | Liu et al. |
| 2021/0022859 A1* | 1/2021 | Crosbie ................ A61F 2/2418 |

\* cited by examiner

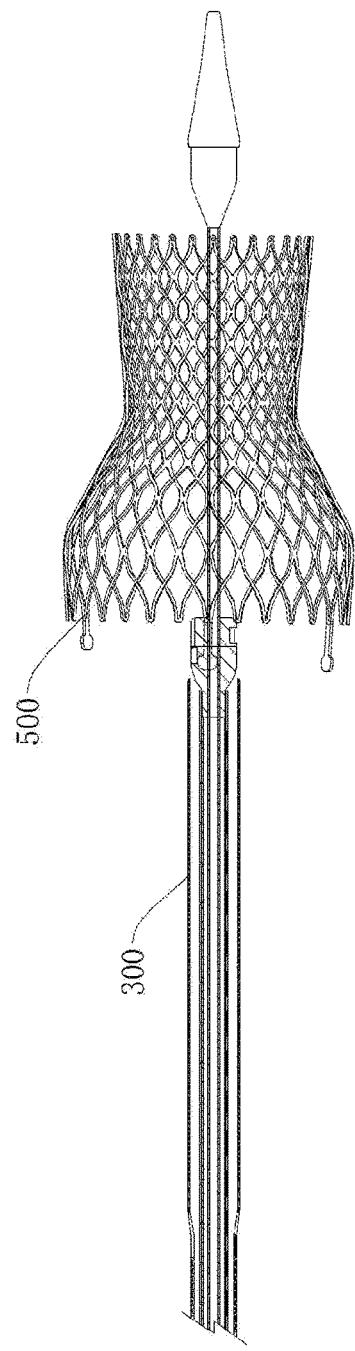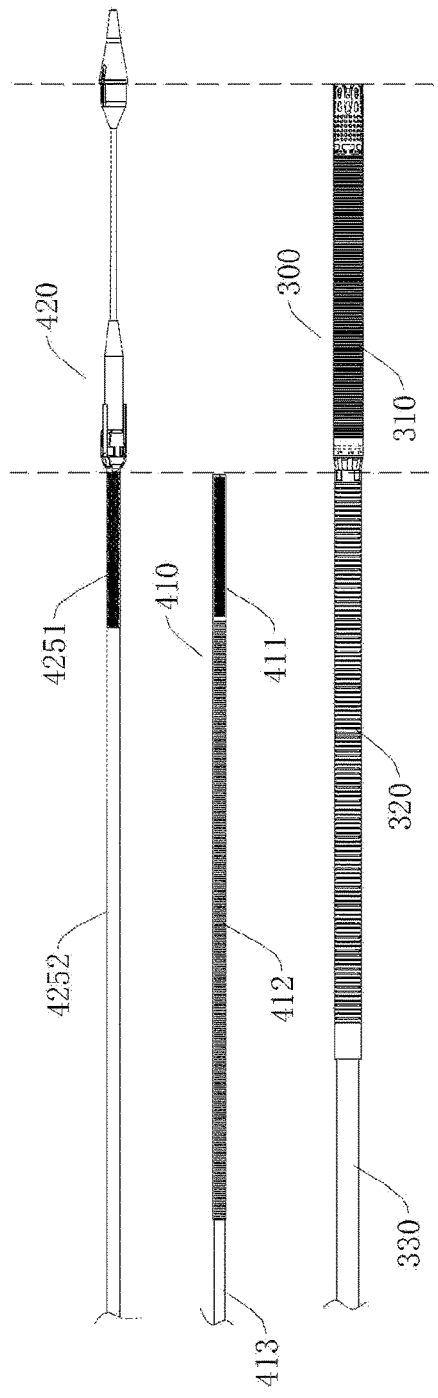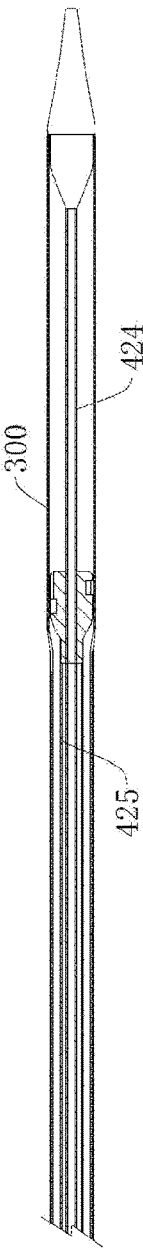

US 11,759,343 B2

DISTAL END STRUCTURE OF SHEATH FOR DELIVERING INTERVENTIONAL INSTRUMENT AND SHEATH

TECHNICAL FIELD

The present invention relates to the technical field of medical devices, and in particular to a distal end structure of a sheath for delivering an interventional instrument, and a sheath.

BACKGROUND

An interventional instrument delivery system generally includes a core assembly and a sheath slidably mounted around an outer periphery of the core assembly, and the two together constitute a sheath assembly, having a distal end able to enter the vascular system of a human and a proximal end connected to an operating handle. Considering the tortuous vascular system of a human being and the long distance that the sheath needs to travel, it is also possible to adjust and control the direction of the distal end according to requirements to move it to a target position.

In some cases, if the interventional instrument is released at an improper position during the operation, the interventional instrument needs to be withdrawn and released again. The distal end of the typical sheath is a loading section that encloses the interventional instrument and usually has a composite structure comprising a metal frame having a membrane covering an inner and/or and outer periphery of the metal frame for sealing and improving the smoothness thereof. The distal end of the sheath has a radially expandable structure, which facilitates the guiding of the expanded interventional instrument at the distal end to be retracted into the sheath again. However, there is a still a need to improve the strength of the expandable structure and the reliability of withdrawal the interventional instrument.

SUMMARY

The present application provides a distal end structure of a sheath, which further ensures the reliability and the strength of the expandable structure.

This application provides a distal end structure of a sheath for delivering an interventional instrument comprising a tubular body section. The body section has opposite distal and proximal sides. A plurality of elastic expansion pieces is arranged circumferentially at the distal side of the body section at intervals. Each expansion piece assumes a converged configuration extending in an axial direction of the body section and a flared configuration away from each other. A connecting strip is provided between two adjacent expansion pieces, and two ends of the connecting strip are respectively connected to expansion pieces at respective sides at connection positions adjacent to distal ends of the expansion pieces.

In the converged configuration of each expansion piece, a middle portion of the connecting strip is folded and received in a region between two adjacent expansion pieces.

In the flared configuration of each expansion piece, the middle portion of the connecting strip is unfolded.

Several alternative implementations are provided below; however, they are not intended to impose additional limitations to the general solution, but are merely further supplemented or preferred implementations. Without technical or logical contradictions, each alternative implementation can be provided individually with respect to the overall solution, or can also be provided in a combination of multiple alternative implementations.

Optionally, a distal lateral edge of each expansion piece has an arc shape, and the connecting strip extends substantially along a tangential direction of the arc and is then connected to the distal lateral edge of a respective expansion piece.

Optionally, two adjacent connecting strips are connected end-to-end at the distal lateral edge of the same expansion piece, and the distal lateral edge at the connection position is smoothly transitioned.

Optionally, all the connecting strips extend continuously in a circumferential direction of the body section.

Optionally, in the converged configuration of each expansion piece, a middle portion of the connecting strip is U-shaped at a proximal side, a bottom of the U-shaped structure has two corner portions, and an outside of each corner portion is provided with a protrusion.

Optionally, an opening is provided between two adjacent expansion pieces; and in the converged configuration of each expansion piece, the connecting strip extends into the opening along an arc-shaped path from its two ends.

Optionally, in the converged configuration of each expansion piece, the proximal side of the connecting strip is in proximity of a middle portion of the opening in the axial direction of the body section.

Optionally, in the flared configuration of each expansion piece, the two protrusions of the same U-shaped structure are adjacent to or abut against each other.

Optionally, in the flared configuration of each expansion piece, the connecting strip has a V-shape, and the apex angle of the V-shape is greater than or equal to 120 degrees.

Optionally, the body section, the expansion pieces and the connecting strips are formed as one piece.

Optionally, in the axial direction of the body section, the opening is widened in the middle portion and narrowed at two ends.

Optionally, each expansion piece has at least one first hollow area, and the expansion pieces are arranged circumferentially, and have a number ranging from 3 to 6.

Optionally, a total area of the at least one hollow area on the same expansion piece is less than 50% of an area of the expansion piece.

Optionally, the at least one hollow area comprises a plurality of through holes, and the through holes on the same expansion piece are arranged on the sheath axially or circumferentially in intervals.

Optionally, a plurality of second hollow areas is provided on a side wall of the body section.

Optionally, the second hollow areas are a plurality of through holes, and the through holes on the body section are randomly arranged or arranged in an array on the peripheral surface.

Optionally, the distal end structure of the sheath is formed by cutting a tube having a shape memory property.

Optionally, the main tube and the head tube are formed as one piece by cutting, or as separate pieces connected end-to-end. Optionally, the proximal side of the body section has a connector that fits to other part of the sheath The present invention further provides a sheath for delivering an interventional instrument, which includes a distal end as a loading section for accommodating the interventional instrument. The loading section has a multi-layer structure and comprises, from the inside to the outside, an inner lining tube, a metal tube and an outer wrapping membrane in sequence, where the metal tube comprises, from a proximal end to a distal end, a main tube and a head tube. The head tube has a distal end structure of a sheath for delivering an interventional instrument as described in the present application.

The present application also provides a sheath for delivering an interventional instrument. The sheath includes, in sequence from a distal end to a proximal end, a loading section, a bendable section, and a first extension section in an axial direction. The sheath has a multi-layer structure, including:

an inner sheath, distributed in the bendable section and the first extension section in the axial direction;

an inner lining tube, connected end-to-end to a distal end of the inner sheath, and distributed in the loading section in the axial direction;

a metal tube, surrounding the distal portion of the inner sheath and the outer periphery of the inner lining tube, and including, from a distal end to a proximal end, a head tube, a main tube, and an extension tube arranged in sequence, wherein in the axial direction, the head tube and the main tube are both distributed in the loading section, and the extension tube is distributed in the bendable section; and wherein the head tube is a distal end structure of a sheath for delivering an interventional instrument as described in this application; and an outer wrapping membrane, wrapped around the outer periphery of the metal tube, and distributed in the bendable section and the loading section in the axial direction.

Optionally, a proximal side of the body section in the distal end structure of the sheath is provided with a first connector, a distal side of the main tube is provided with a second connector, and the first connector and the second connector are fitted with each other through form-fitting.

Optionally, the first connector and the second connector are both T-shaped.

Optionally, a wall of the metal pipe is provided with a through hole, through which the inner lining tube and the outer wrapping membrane are heat-melted and/or bonded to each other.

The distal end structure of a sheath according to this application has a radially expandable structure. By means of multiple metal sheets, i.e., the expansion pieces, guiding of the withdrawal of the interventional instrument can be achieved while the strength is ensured. Further, the reliability can be ensured by the connecting strips, to avoid the insertion of the expansion pieces into the structural gap of the interventional instrument.

BRIEF DESCRIPTION OF THE DRAWINGS

FIG. 2b is an exploded view of the interventional instrument delivery system in FIG. 2a;

FIG. 3a is a schematic view showing the internal structure of an operating handle in FIG. 2a;

FIG. 3b is partially enlarged view of a front handle portion in FIG. 3a;

FIG. 4 is an exploded view of the operating handle in FIG. 2a;

FIG. 15c is a schematic structural view showing the interventional instrument in FIG. 15a completely released;

FIG. 15d is a schematic view illustrating the relationships between the axial sections of each tube according to an embodiment of the present application;

FIG. 16 is a cross-sectional view showing a sheath and a core tube component according to an embodiment of the present application;

Figure 1A:
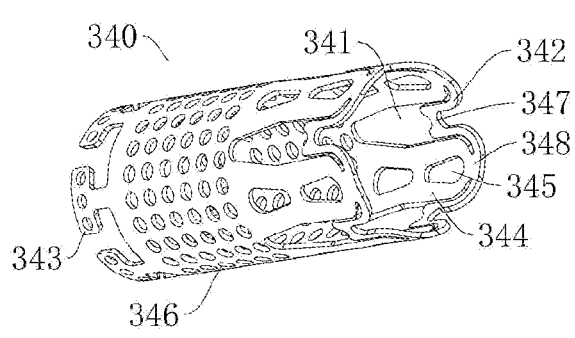
FIGS. 1a to 1b are schematic structural views of different aspects of the expansion pieces in a converged configuration in a distal end structure of a sheath according to one embodiment of the present application.

LIST OF REFERENCE NUMERALS 100. operating handle;
110. bending adjustment component; 111. second support; 112. second driving member; 113. second connecting part; 114. guide bar; 115. guide groove; 116. operating port; 117. force applying portion; 118. Luer fitting;
120. control component; 121. first support; 122. first driving member; 123. first connecting part; 124. guide key; 125. guide slot; 126. eyelet;
130. front handle; 131. sliding key; 132. sliding chute;
200. catheter;
300. sheath; 310. loading section; 320. bendable section; 330. first extension section; 340. head tube; 341. opening; 342. connecting strip; 342a. connecting strip; 342b. connecting strip; 343. first connector; 344. expansion piece; 345. hollow area; 346. body section; 347. middle portion; 348. distal lateral edge; 349. protrusion; 350. main tube; 351. second connector; 360. extension tube; 3601. reinforcing rib; 3602. reinforcing rib; 370. inner sheath; 3701. PTFE inner layer; 3702. woven layer; 3703. reinforcing rib; 3704. woven layer; 3705. outer layer; 380. outer wrapping membrane;
400. core assembly;
410. bendable adjustable tube; 411. first pulling section; 4111. reinforcing rib; 412. second pulling section; 4121. reinforcing rib; 4122. reinforcing rib; 413. second extension section; 414. transition section;
420. core tube component; 421. guide head; 422. locking member; 4221. eyelet; 4222. wire distribution disc; 4223. pull wire; 4224. latching rod; 4225. wire running sleeve; 423. pressing strip; 424. inner core; 425. core tube; 4251. compliant section; 4252. third extension section; 4253. reinforcing rib;
500. interventional instrument; 501. connecting lug.

DESCRIPTION OF THE EMBODIMENTS

The technical solutions according to the embodiments of the present application will be described clearly and fully in combination with the accompanying drawings in the embodiments of the present application. The embodiments described are merely some but not all of the embodiments of the present application. All other embodiments obtained by persons of ordinary skill in the art based on the embodiments of the present application without creative efforts shall fall within the scope claimed by the present application.

It should be noted that when a component is described to be "connected" to another component, it may be directly connected to another component or may be indirectly connected to another component through an intermediate component. When a component is "provided on" another component, it may be directly provided on another component or may be provided on another component through an intermediate component.

Unless otherwise defined, all technical and scientific terms used herein have the same meaning as commonly understood by persons skilled in the art. The terms used in the descriptions of the present application are for the purpose of describing specific embodiments only and are not intending to limit the present application. The term "and/or" as used herein includes any combinations of one or more of the listed options, as well as the combination of all of the listed options.

In an interventional operation, if an interventional instrument is released at an improper position, the interventional instrument often needs to be withdrawn and released again. The typical sheath has a plurality of radially expandable expansion pieces at a distal end thereof, which facilitates guiding of the expanded interventional instrument at the distal end to be retracted into the sheath again. In practice, there are cases where the interventional instruments fail to be withdrawn. Analysis shows that these interventional instruments often have large structural gaps (for example, the grids are relatively sparse), and the expansion piece may be occasionally inserted into the structural gap of the interventional instrument when withdrawn, which prevents movement of the interventional instrument, and therefore the interventional instrument cannot be retracted into the sheath.

The present application provides a distal end structure of a sheath according to one embodiment. The distal end structure of the sheath, as a distal portion, i.e., a head tube 340, of the sheath, is only a metal frame portion. In use, it is connected to another portion (proximal portion) of the sheath, and then is provided with a membrane to generally ensure the necessary protection and sealing.

In this embodiment, the distal end structure of the sheath includes a tubular body section 346. The body section 346 has opposite distal and proximal ends. A plurality of expansion pieces 344 are arranged in intervals at the distal end of the body section 346 in a circumferential direction. Each expansion piece 344 assumes a converged configuration extending in an axial direction of the body section 346 and a flared configuration away from each other. A connecting strip 342 is provided between two adjacent expansion pieces, and two ends of the connecting strip 342 are connected to expansion pieces 344 at respective sides at connection positions adjacent to distal ends of the expansion pieces 344.

Figure 1B:
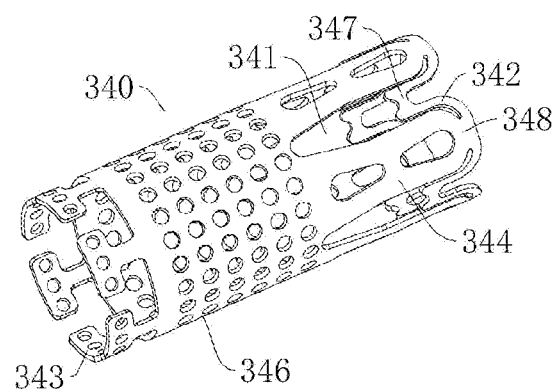

Referring to FIGS. 1a and 1b, in the converged configuration of each expansion piece 344, a middle portion 347 of the connecting strip 342 is folded and received in a gap between the two adjacent expansion pieces.

Figure 1C:
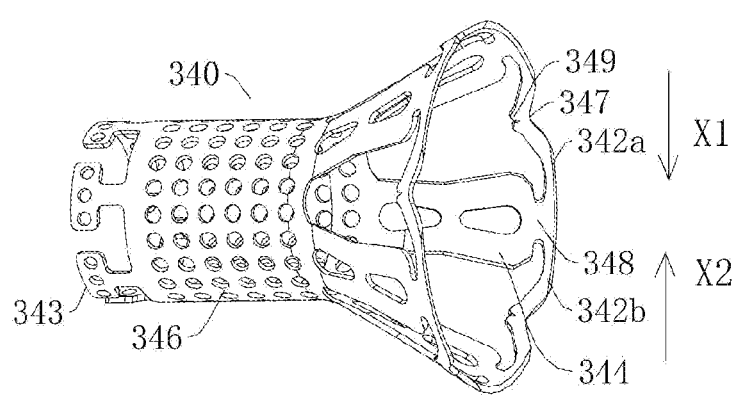
FIGS. 1c-1d are schematic structural views of different aspects of the expansion pieces in a flared configuration in a distal end structure of a sheath according to one embodiment of the present application.
Figure 1D:
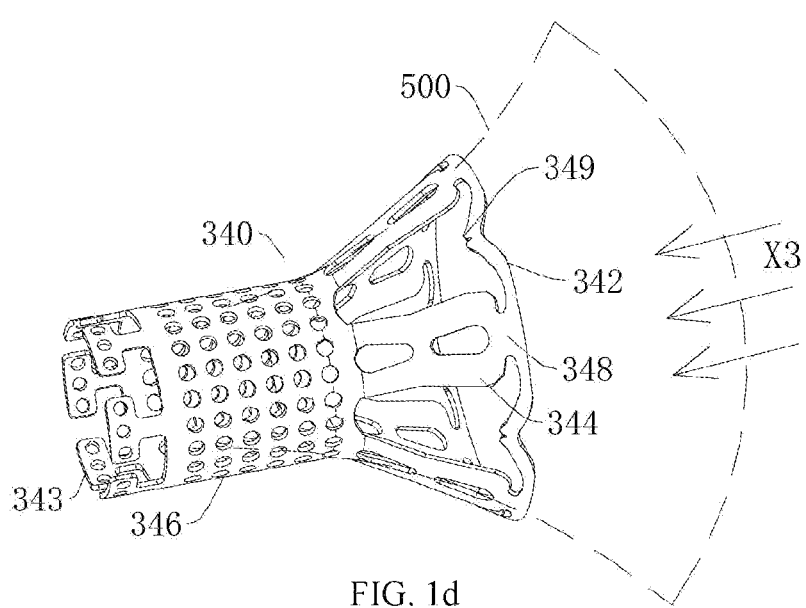
Figure 2A:
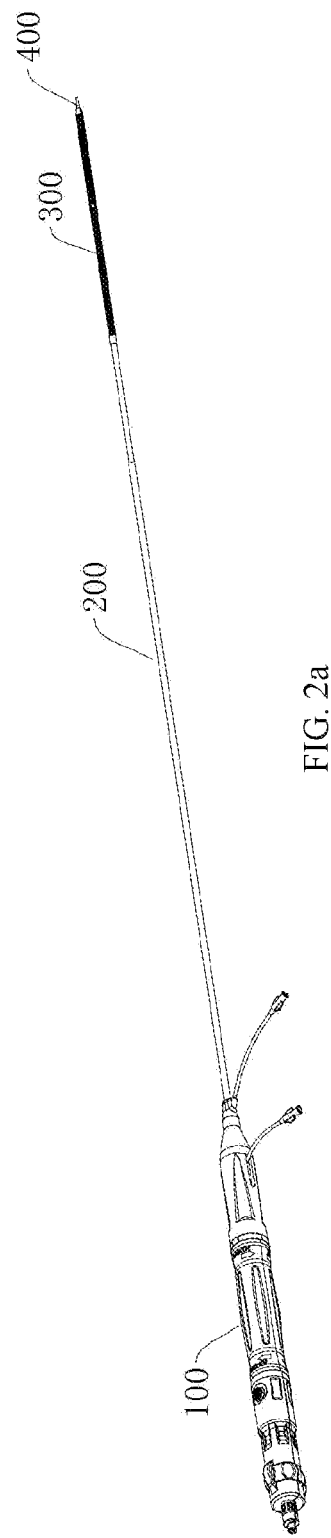
FIG. 2a is a schematic structural view of an interventional instrument delivery system using a distal end structure of a sheath according to the present application.
Figure 2B:
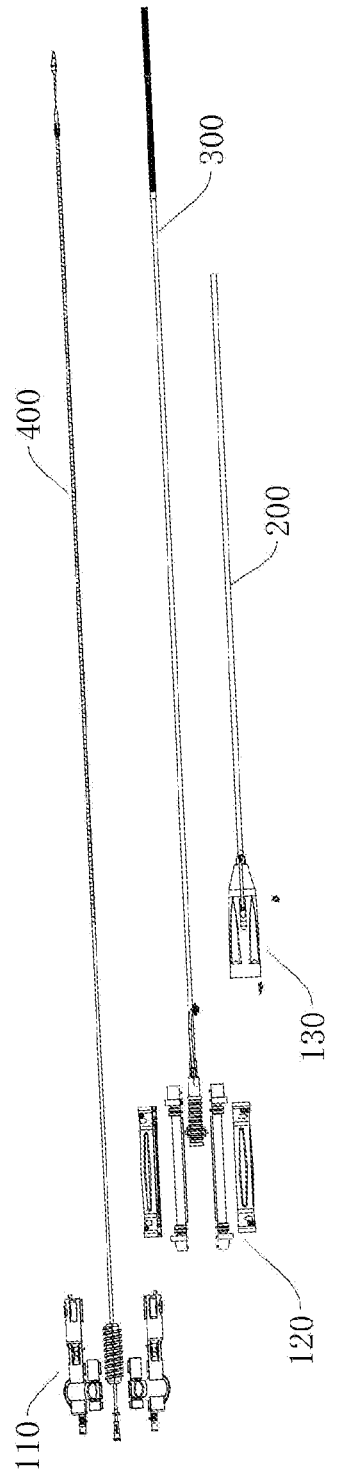

Referring to FIGS. 1c and 1d, in the flared configuration of each expansion piece 344, the middle portion 347 of the connecting strip 342 is relatively unfolded, relative to the converged configuration.

In the prior art, the distal ends of each expansion piece 344 are isolated, which may be inserted into the structural gap of the interventional instrument 500, preventing the withdrawal of the interventional instrument. Moreover, the radial contraction force of each expansion piece 344 in the flared configuration is insufficient, leading to poor performance in guiding the contraction of the interventional instrument 500.

In this embodiment, the distal end structure, i.e., the head tube 340, of the sheath is further improved by providing a connecting strip 342 between two adjacent expansion pieces 344. The connecting strip 342 may be a single strip or double-strips or a structure having grids or a hollow area. In general, the connecting strip is connected between two adjacent expansion pieces 344. Particularly, in the flared configuration, the connecting strip 342 additionally provides a pulling force between the two expansion pieces 344, to strengthen the radial binding force to all expansion pieces 344 and to improve the guiding and withdrawal for the interventional instrument 500. The interventional instrument 500 is withdrawn and retracted into the sheath along a direction X3. More importantly, the connecting strip 342 is connected to the expansion pieces 344 at positions adjacent to the distal ends of expansion pieces 344, thus eliminating isolated tip or spike structures of expansion pieces 344 and avoiding them piercing into the structural gap of the interventional instrument 500.

The connection position between each end of the connecting strip 342 and the respective expansion piece 344 at each respective side is adjacent to the distal end of the expansion piece 344, and can be understood as that the connection position is located adjacent to or at the distal end of the expansion piece 344. This can prevent the distal end of the expansion piece 344 from forming an isolated protruding portion especially in the flared configuration, thus reducing the risk of interference with the interventional instrument.

The shape of the middle portion 347 is not limited to that shown and described herein. It mainly functions to connect and pull the two expansion pieces 344 in the flared configuration. The middle portion 347 has a foldable structure as it needs to be folded and collapsed in the converged configuration. The folding process can be driven by the elasticity of the expansion piece 344. Alternatively, it is also possible that the middle portion 347 itself is formed of a pre-shaped elastic material to facilitate the folding. After being folded, the middle portion is received between the two adjacent expansion pieces, and extends towards the proximal end accordingly.

The connection between the expansion piece 344 and the connecting strip 342 affects the stress distribution and the folding of the connecting strip 342. In one embodiment, a distal lateral edge 348 of each expansion piece 344 has an arc shape, and the connecting strip extends substantially along a tangential direction of the arc and is then connected to the distal lateral edge of the adjacent expansion piece. Referring to FIG. 1c, two adjacent connecting strips 342a and 342b are shown, wherein the connecting strip 342a extends in the direction X1 towards the distal lateral edge 348 of the expansion piece 344, the connecting strip 342b extends in the direction X2 towards the distal lateral edge 348 of the expansion piece 344, and the connecting strip 342a and the connecting strip 342b merge with each other into a whole.

The arc shape of the distal lateral edge 348 merely indicates a general trend or the overall shape characteristics, which is not intended to be limited to what is shown or described herein. The connecting strips extend and merge in the tangential direction, providing a better radial gathering force with a more reasonable stress distribution.

In another embodiment, two adjacent connecting strips are connected end-to-end at the distal lateral edges of the same expansion piece, and the distal lateral edges at the connecting position is smoothly transitioned. The smooth outer edges can avoid potential injury to the patient. For example, the connecting strip 342a and the connecting strip 342b are connected end-to-end at the distal lateral edge 348 of the same expansion piece 344 and merge into a whole after connecting. The connecting position is relatively smooth to avoid the interference with the interventional instrument 500 by a spike or protruding part.

Furthermore, all the connecting strips extend continuously in the circumferential direction of the body section 346. As can be seen from the figures, because adjacent connecting strips are smoothly connected, all the connecting strips are connected to form a ring. Although there are undulations at the middle portions 347, this does not affect the overall trend.

In one embodiment, in the converged configuration of each expansion piece, the middle portion 347 of the connecting strip 342 is U-shaped at the proximal end, the bottom of the U-shaped structure has two corner portions, and the outside of each corner portion is provided with a protrusion 349. The protrusion 349 can strengthen the structure of the corner portion to avoid fatigue damage caused by repeated bending.

In one embodiment, in the flared configuration of each expansion piece, the two protrusions of the same U-shaped structure are adjacent to or abut against each other. The two protrusions adjacent to or abutting against each other can limit the deployment angle of the connecting strip 342, to avoid reverse folding under extreme or abnormal conditions.

In one embodiment, there is an opening 341 between two adjacent expansion pieces. In the converged configuration of each expansion piece, the connecting strip 342 extends into the opening 341 along an arc-shaped path from its two ends. In other words, the connecting strip 342 is arc-shaped at the distal lateral edge 348 adjacent to the expansion piece 344, to better follow the shape of the expansion piece 344, and to extend in proximity to the edge of the expansion piece 344 so as to occupy less space. When unfolded, the arc structure will not suffer from excessive stress concentration, thereby reducing the safety hazards caused by fatigue fracture.

In the converged configuration of each expansion piece, the proximal end of the connecting strip 342 is located adjacent to the middle portion of the opening 341 in the axial direction of the body section 346. In the converged configuration of each expansion piece, the opening 341 is substantially an elongated notch, having a distal end closed by the connecting strip 342 and a proximal end closed by the body section 346. The head tube 340 may be made of elastic metal materials such as Nitinol. In other words, it is preferred that the body section, the expansion pieces and the connecting strips are integrally formed in one piece. Therefore, each expansion piece 344 can be radially flared outwardly to adapt to the gradual transformation of the interventional instrument when the interventional instrument is released, and prevent the interventional instrument from suddenly popping out at the end of the release. Further, when withdrawn, the expansion pieces 344 are radially flared to form a flared opening, which is convenient for guiding the interventional instrument to be gradually compressed radially and retracted in the sheath 300.

The connecting strip 342 determines the extension position of the proximal end after being folded. In the axial direction of the body section 346, the relationship between the lengths of the opening 341 and the connecting strip 342 affects the extreme flaring angle of the expansion piece 344. Therefore, a suitable relationship contributes to the control of the spatial posture of the expansion piece 344 during release or withdrawal, and ensures the control of the shape of the interventional instrument.

In the flared configuration of each expansion piece, the connecting strip 342 is substantially V-shaped, and the apex angle of the V-shaped structure is greater than or equal to 120 degrees. Of course, in view of the foregoing, the apex angle of the V-shape may assume a rounded structure, and thus is substantially U-shaped.

In one embodiment, each expansion piece has a hollow area. The expansion pieces are arranged in the circumferential direction. The number of the expansion pieces ranges from 3 to 6, for example five expansion pieces may be provided.

The hollow area 345 of the expansion piece 344 facilitates the deformation of the expansion piece, and reduces the flaring resistance. In one embodiment, the hollow area 345 may be an elongated hole, a round hole, or have the shape of an ellipse or a tear drop. On the same expansion piece, one or several hollow areas 345 separated from each other may be provided. An inner edge of each hollow area is smooth to avoid cracking caused by excessive stress concentration during deformation. The total area of the hollow areas on each expansion piece is less than 50% of the area of the expansion piece. The hollow areas 345 may include a plurality of through holes, and the through holes on the same expansion piece may be arranged in intervals along the axial or circumferential direction of the sheath.

The body section 346 may also have a hollow imagining area, where imaging points are provided, to monitor the position or posture of the instrument by an imaging device during the operation.

In the subsequent processing, it is also possible that both the radial inner side and radial outer side of the body section 346 are each provided with a membrane. To facilitate the fusion of the inner and outer membranes, a plurality of second hollow areas is provided on the side wall of the body section. The second hollow areas include a plurality of through holes, which may be arranged randomly or arranged in an array on the peripheral surface.

In the axial direction of the body section 346, the opening 341 is widened in the middle portion and narrowed at its two ends. The expansion piece 344 is gradually widened closer to its proximal end to increase the connection strength and ensure the necessary resilience. The opening 341 has an arc-shaped boundary at the most proximal end to decentralize the stress and improve the safety.

The proximal side of the body section 346 has a connector, for example, a T-shaped first connector 343, that fits to other part of the sheath. Both the body section 346 and the first connector 343 are provided with through holes, to allow a polymer material as the inner and outer membranes of the sheath to be better fused to each other.

On the whole, the distal end structure of the sheath is cut from a tube having a shape memory property which is made of, for example, Nitinol.

Referring to FIGS. 2*a* to 4, the present application provides an interventional instrument delivery system according to one embodiment, which has opposite distal and proximal ends. The delivery system includes an operating handle 100 at the proximal end, and a sheath assembly connected to the operating handle 100 and extending towards the distal end. The sheath assembly includes a sheath 300 and a core assembly 400.

The core assembly includes a core tube, and a locking member coupled to the distal end of the core tube and configured to connect an interventional instrument.

The sheath 300 is slidably fitted around an outer periphery of the core assembly 400. A distal end of the sheath serves as a loading section which is configured to receive the interventional instrument.

A plurality of elastic expansion pieces 344 (see FIG. 1*a* to FIG. 1*d*) are arranged circumferentially in intervals at a distal side of the loading section. Each expansion piece 344 can assume a converged configuration extending in an axial direction of the body section 346 and a flared configuration away from each other. A connecting strip 342 is provided between two adjacent expansion pieces, and two ends of the connecting strip 342 are respectively connected to expansion pieces 344 at respective sides at connection positions adjacent to distal ends of the expansion pieces 344.

Referring to FIGS. 1*a* and 1*b*, in the converged configuration of each expansion piece 344, a middle portion 347 of the connecting strip 342 is folded and received in a region between the two adjacent expansion pieces.

Referring to FIGS. 1*c* and 1*d*, in the flared configuration of each expansion piece 344, the middle portion 347 of the connecting strip 342 is unfolded relative to the converged configuration.

For the sheath 300, the distal end structure of the sheath according to the above embodiments can be used. For the specific structure of the sheath itself, some improved embodiments are provided below.

The locking member of the core assembly may be embodied in various forms, for example, a groove which is configured for connecting a connecting lug on a stent, a protrusion head that protrudes radially outwardly, or a wire-controllable means in which a long wire or wire loop is connected to the stent. Regardless of what structure is used, the purpose is to establish the connection between it with the connecting lug on the stent.

In some embodiments, the core assembly further includes a bending adjustment mechanism mounted around an outer periphery of the core tube. The bending adjustment mechanism can drive the distal end of the core tube to move, changing the orientation of the core tube to adapt to the position for deploying the interventional instrument.

In some embodiments, the bending adjustment mechanism is a bendable adjustable tube. The distal ends of the bendable adjustable tube and the core tube are fixedly connected to each other, and their proximal ends extend to and are connected to the operating handle, and are slidable relative to each other.

In some embodiments, the core assembly further includes a bendable adjustable tube in the core tube. The distal ends of the bendable adjustable tube and the core tube are fixedly connected to each other, and their proximal ends extend to and are connected to the operating handle, and are slidable relative to each other.

Regardless of the radial-positional-relationship between the core tube and the bendable adjustable tube, relative movement of their proximal ends is required. Generally, upon bending adjustment, the position of the proximal end of the core tube is maintained fixed, or is taken as a reference, and the proximal end of the bendable adjustable tube is pulled. Different radial-positional-relationships between the core tube and the bendable adjustable tube cause the two to abut at different positions at a turning site. In the following embodiments and drawings, examples are given with the bendable adjustable tube located on the outside. The structure of the operating handle can be adapted correspondingly according to the radial-positional-relationship between the core tube and the bendable adjustable tube, so that their proximal ends can move relative to each other.

In other embodiments, the interventional instrument delivery system may further include a catheter 200 that is fixed relative to the operating handle 100. The catheter 200 serves to establish a channel to prevent injury to tissues in the body when the sheath 300 moves back and forth. The interventional instrument is loaded on the core assembly 400 and enclosed by the sheath 300, and then enters the body with the catheter 200. The sheath 300 can move axially relative to the interventional instrument and the core assembly 400 to release the interventional instrument and to be withdrawn when necessary.

The bending adjustment is mainly performed by controlling the operating handle 100. In an embodiment shown in FIGS. 3a to 4, the operating handle 100 is configured to connect the proximal ends of the three tubes which are sequentially nested within each other from the inside to the outside, and drive the proximal ends of the three tubes to move relative to each other. The three tubes are respectively, from the inside to the outside, the core tube, the bendable adjustable tube and the sheath. The operating handle 100 includes a control component 120, a bending adjustment component 110 and a front handle 130.

The control component 120 includes:
a first support 121 fixed relative to the front handle 130;
a first connecting member 123 slidably mounted to the first support 121, wherein the proximal end of the sheath is fixed to the first connecting member 123; and
a first driving member 122 movably mounted to the first support 121 and configured for driving the first connecting member 123 to slide.

The bending adjustment component 110 includes:
a second support 111 fixed relative to the first support 121;
a second connecting member 113 slidably mounted to the second support 111, wherein the proximal end of the bendable adjustable tube extends out of the sheath and is then fixed to the second connecting member 113;
a second driving member 112 movably mounted to the second support 111 and configured for driving the second connecting member 113 to slide; and
a tube fitting fixedly mounted at a proximal end of the second support 111, wherein the proximal end of the core tube extends out of the bendable adjustable tube and is then fixed to the tube fitting.

Of course, when the bendable adjustable tube is not provided, the bending adjustment component 110 is omitted accordingly, and the operating handle 100 is further simplified.

Specifically, the control assembly 120 includes the first support 121. The first driving member 122 is rotatably mounted around the outer periphery of the first support 121. A side wall of the first support 121 is provided with a guide slot 125 extending in the axial direction. The first connecting member 123 is slidably mounted inside the first support 121, and the first connecting member 123 is provided with a guide key 124 extending out of the guide slot 125. An inner wall of the first driving member 122 has a screw thread for engaging with the guide key 124.

As for the configuration of the first support 121, according to one embodiment, the first support 121 is cylindrical, the side wall of the first support 121 is provided with the guide slot 125 extending in the axial direction, and the first connecting member 123 is slidably mounted inside the first support 121. The first connecting member 123 is provided with the guide key 124 extending radially out of the guide slot 125, and the inner wall of the first driving member 122 has a thread engaging with the guide key 124.

Figure 4:
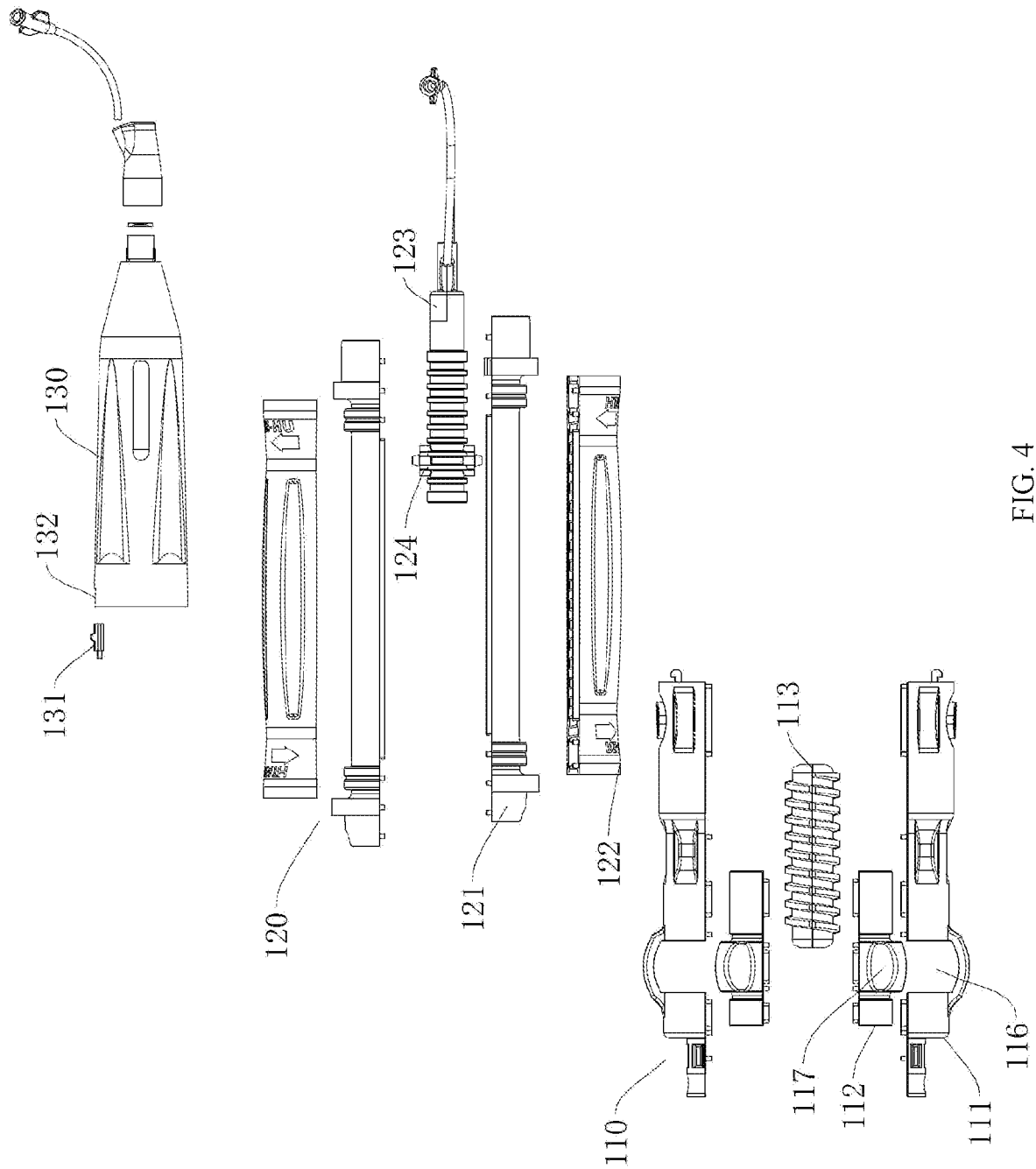

Specifically, the first support 121 is substantially cylindrical, and may be configured as one single piece, or has a plurality of separate pieces radially snap-fit with each other (as shown in FIG. 4). When the first driving member 122 rotates, the first connecting member 123 is driven by the guide key 124 to slide inside the first support 121. Due to the restriction by the guide slot 125, the first connecting member 123 only moves axially without rotation.

The front handle 130 is fixedly connected to the first support 121, and the proximal end of the catheter 200 is fixedly inserted in the front handle 130. The proximal end of the sheath 300 is fixedly mounted to the first connecting member 123, and the sheath 300 extends distally through the catheter 200.

As for the mating relationship between the first support 121 and the second support 111, according to one embodiment, the second support 111 is cylindrical and arranged coaxially with the first support 121. The second support 111 and the first support 121 may be formed as one single piece or as separate pieces which are fixed together.

For the mating relationship between the second driving member 112 and the second support 111, according to one embodiment, the second driving member 112 is rotatably mounted relative to the second support 111. The second support 111 is provided with an operating port 116; and a portion of the second driving member 112 is positioned inside the second support 111, and at least another portion of the second driving member 112 is exposed from the operating port 116 to serve as a force applying portion 117. The second connecting member 113 is located inside the second support 111 and moves in association with the second driving member 112.

Specifically, the bending adjustment component 110 includes the second support 111, which is substantially cylindrical and fixed relative to the first support 121. The second support 111 may be formed as one single piece or may have separate pieces which are radially snap-fitted (as shown in FIG. 4). The second support 111 and the first support 121 are formed as separate elements which are coaxially arranged and connected end-to-end.

Correspondingly, the bending adjustment component 110 further includes the second driving member 112. For the specific configuration of the second driving member 112, according to an embodiment, the second driving member 112 has internal screw threads, and at least a portion of the second connecting member 113 is provided with external screw threads and extends into the second driving member 112. As a result, the second driving member 112 can drive the second connecting member 113 to slide through the threaded connection.

Specifically, the second driving member 112 is rotatably mounted relative to the second support 111. The second support 111 is partially provided with the operating port 116; and a portion of the second driving member 112 is positioned inside the second support 111, and at least another portion of the second driving member 112 is exposed from the operating port 116 and serves as the force applying portion 117. The second driving member 112 is substantially cylindrical and has internal screw threads, and the second connecting member 113 is slidably mounted in the second driving member 112.

To restrain the movement of the second connecting member 113, according to one embodiment, an inner wall of the second support 111 is provided with a guide bar 114 extending in the axial direction, at least a portion of the second connecting member 113 is located in the second support 111, and an outer wall of this portion is provided with a guide groove 115 corresponding to the guide bar 114. In this embodiment, the guide bar 114 is retained in the guide groove 115 such that the second connecting member 113 can only slide axially relative to the second support 111.

It is understandable from the above descriptions that the bending adjustment of the operating handle 100 is mainly achieved by the rotation of the respective components. In order to prevent unstable bending adjustment caused by the relative movement of each component during the operation, a limiting mechanism may be provided. According to an embodiment, the first driving member 122 is rotatably mounted around the outer periphery of the first support 121, and a limiting mechanism for restraining the rotation angle of the first driving member 122 is provided between the front handle 130 and the first driving member 122.

Accordingly, this embodiment provides one exemplary form of the limiting mechanism. In this embodiment, the limiting mechanism includes: a sliding key 131 mounted in either the front handle 130 or the first driving member 122; and an eyelet 126, provided in the other one of the front handle 130 and the first driving member 122.

When the sliding key 131 is engaged with the eyelet 126, the positions of the front handle 130 and the first driving member 122 in the circumferential direction are determined. Therefore, the axial position of the first connecting member 123 relative to the front handle 130 is determined, and the bending adjustment function of the operating handle 100 is locked, ensuring the stability during use. In one specific embodiment, an outer wall of the front handle 130 is provided with a sliding chute 132. The sliding key 131 is mounted in the sliding chute 132, and the eyelet 126 is provided in an axial end surface of the first driving member 122.

Figure 3A:
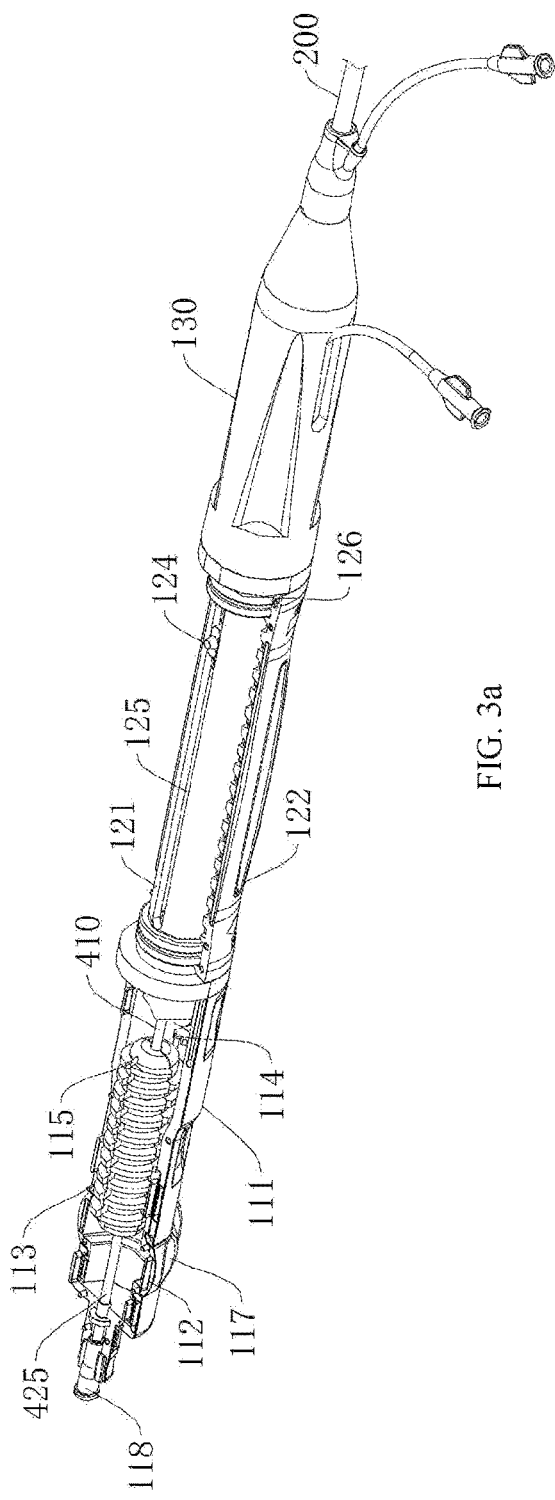
Figure 3B:
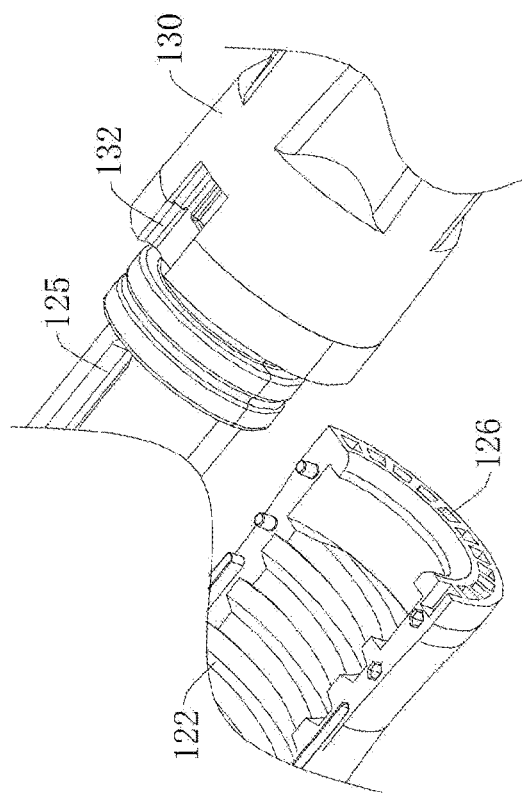

It is possible to lock the first driving member 122 at multiple positions by increasing the number of the eyelets 126. Referring to FIG. 3b, a plurality of eyelets are provided in the axial end surface of the first driving member 122, which are arranged sequentially along the circumferential surface of the first driving member 122. The increase in the number of eyelets 126 can increase the locking positions of the first driving member 122. However, the increase in the number of eyelets 126 will increase the difficulty in manufacturing the first driving member 122 and reduce the distance between adjacent eyelets 126, thereby reducing the strength of individual eyelets 126. Therefore, the specific number can be adjusted according to the design requirements, practical working conditions, and actual product size.

Because the first driving member 122 includes separate upper and lower pieces that are snap-fitted together, there are two options for the eyelet 126 near the separation face. In one option, the eyelet is opened toward the separation face, and in the other option, the eyelet is designed to avoid the separation face and has a closed form. Either one of the two options can be used for any specific product.

Correspondingly, a limiting mechanism may also be provided between the first driving member 122 and the first support 121 to achieve the above-mentioned functions. In one embodiment, the limiting mechanism includes a locking pin (not shown) that is screwed on the first driving member 122 and abuts against the first support 121. The locking pin is screwed to the first driving member 122, and thus the position of the locking pin relative to the first driving member 122 is determined, thereby achieving the positioning of the first support 121. When the relative positions of the first driving member 122 and the first support 121 are determined, the function of the above-mentioned limiting mechanism is achieved, and the locking principle will not be further described herein.

The present application provides a core assembly according to one embodiment for delivering an interventional instrument, which includes a core tube, a locking member fixed at a distal end of the core tube for connecting the interventional instrument, and a bendable adjustable tube mounted around an outer periphery of the core tube. The distal ends of the bendable adjustable tube and the core tube are fixedly connected to each other, and the proximal ends of the bendable adjustable tube and the core tube can slide relative to each other. The core assembly 400 includes the bendable adjustable tube 410 and a core tube 425 nested within each other. The bendable adjustable tube 410 surrounds the outside of the core tube 425, with their distal ends fixedly connected to each other, and their proximal ends can slide relative to each other. The proximal end of the bendable adjustable tube 410 is fixed to the second connecting member 113, and the proximal end of the core tube 425 extends out of the second connecting member 113 and is then fixed to a tail, that is, the proximal end, of the second support 111. To facilitate the connection with an external tube, the proximal end of the core tube 425 is provided with a tube fitting, such as a Luer fitting 118.

When the interventional instrument needs to be released or withdrawn, the first driving member 122 is rotated to allow the first connecting part 123 to move axially, and drive the sheath 300 to move relative to the core assembly 400. When bending adjustment is required, the second driving member 112 is rotated to move the second connecting part 113 axially, and drive the proximal end of the bendable adjustable tube 410 to move relative to the proximal end of the core tube 425. Because the distal ends of the bendable adjustable tube 410 and the core tube 425 are fixed relative to each other, the relative movement of their proximal ends will cause their distal ends to deflect and curve radially together.

Referring to FIGS. 5a to 11, the core assembly 400 includes the bendable adjustable tube 410 and a core tube component 420. The core tube component 420 includes the core tube 425, and the locking member 422 is mounted at the distal end of the core tube 425 and configured to connect the interventional instrument. The bendable adjustable tube 410 is mounted around the outer periphery of the core tube 425. The distal ends of the bendable adjustable tube 410 and the core tube 425 are fixedly connected to each other, and the proximal ends of the bendable adjustable tube 410 and the core tube 425 can slide relative to each other.

The distal end of the bendable adjustable tube 410 extends to a position adjacent to a proximal end of the locking member 422. The bendable adjustable tube 410 may be directly fixed to the core tube 425, or the locking member 422, or both. The bendable adjustable tube 410 and the core tube 425 both may be made of metal materials such as hypotubes, and they can be fixed by welding, bonding or by a fastener.

The distal end of the core tube 425 further extends out of the locking member 422 and is fixed to a guide head 421. A distal end of the guide head 421 has a conical-shaped head to facilitate travel within the body. A position between the guide head 421 and the locking member 422 is configured as a loading position of the interventional instrument. The compressed interventional instrument is located at this position, fitted to and restrained by the locking member 422.

In one embodiment, the core tube 425 is provided with an inner core 424 extending therein. A distal end of the inner core 424 extends out of the locking member 422 and is fixed to the guide head 421. The extension length of a proximal end of the inner core 424 is not strictly limited. A position on the outer periphery of the inner core 424 between the guide head 421 and the locking member 422 is formed as the loading position of the interventional instrument. The compressed interventional instrument is located at this position and fitted to and restrained by the locking member 422. Since the core tube 425 does not extend to the loading position, and the inner core 424 has a smaller outer diameter compared with the core tube 425, so the radial space at the loading position is increased.

Figure 5B:
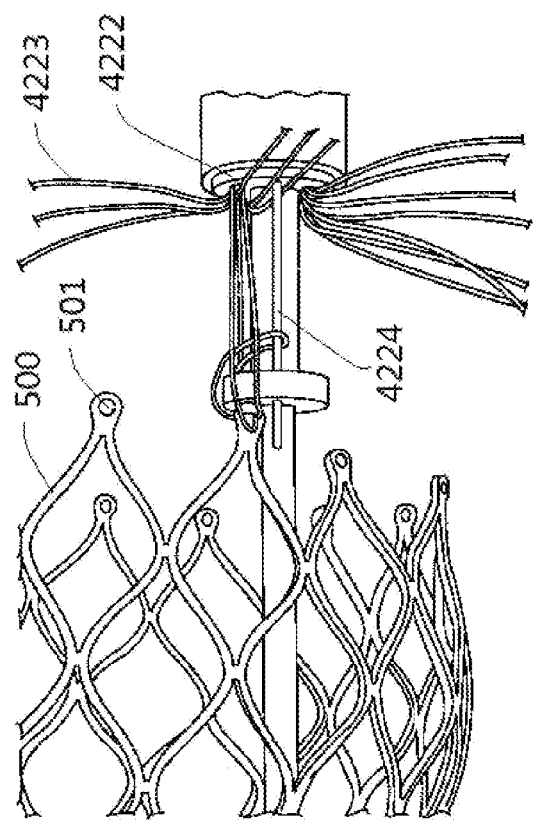
FIG. 5b is a schematic view showing the locking member in FIG. 5a fitted with an interventional instrument.
Figure 5A:
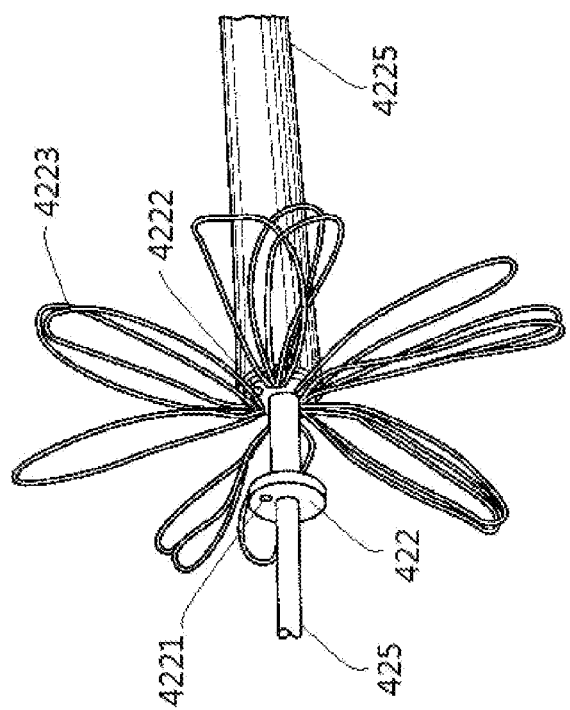
FIG. 5a is a schematic structural view showing a locking member of a core assembly adopting a wire control means according to an embodiment of the present application.

Referring to FIGS. 5a and 5b, in some embodiments, the locking member is a wire-controlled means. The proximal end of the interventional instrument 500 has a connecting lug 501. The connecting lug 501 generally has a hole or hook through which a pull wire 4223 extends. The locking member 422 has an eyelet 4221. A distal end of a latching rod 4224 is fitted with the eyelet 4221, and a proximal end of the latching rod 4224 may extend to the operating handle.

In a loaded state, the pull wire 4223 extends through the connecting lug 501 and then is connected to the locking rod 4224. Since the distal end of the locking rod 4224 is inserted into the eyelet 4221, the connecting lug 501 is restrained by the pull wire 4223 from releasing from the locking member 422. When the interventional instrument needs to be released, the locking rod 4224 is pulled toward the proximal end and then released from the eyelet 4221, and thus the pull wire 4223 is released, allowing the connecting lug 501 to disconnect from the locking member 422.

When a plurality of connecting lugs 501 are provided, a corresponding plurality of pull wires 4223 are provided. The pull wires 4223 are respectively extended distally through a wire distribution disc 4222. To organize the pull wires, a wire running sleeve 4225 may be provided, which is mounted around the outer periphery of the core tube 425 with a passage formed therebetween through which the pull wires 4223 extend.

The engageable latching rod 4224 and eyelet 4221 together form a set of latching mechanisms. Multiple sets of latching mechanisms can be provided as required, which are arranged in sequence along the circumferential direction of the locking member 422.

Figure 5C:
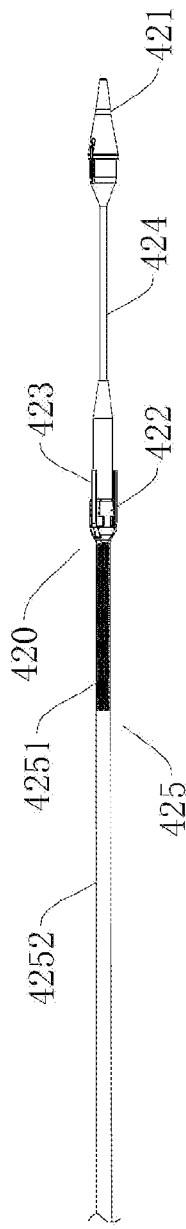
FIG. 5c is a schematic structural view of a core tube component according to an embodiment of the present application.
Figure 6:
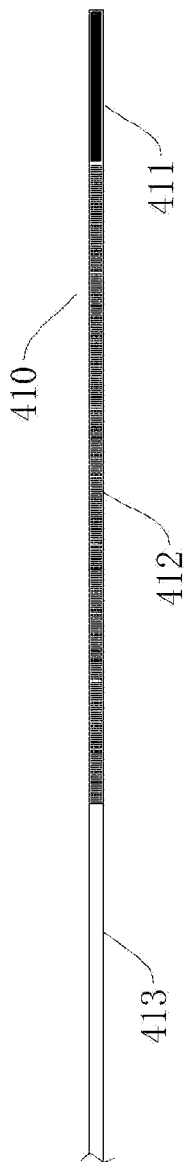
FIG. 6 is a schematic structural view of a bendable adjustable tube according to an embodiment of the present application.

Referring to FIG. 5c, in some embodiments, one or more limiting grooves are provided on the outer periphery of the locking member 422, and the interventional instrument has one or more connecting lugs inserted into the one or more limiting grooves. The limiting groove is configured for limiting the interventional instrument in the axial position, and only allows the interventional instrument to be released after radial expansion. To prevent the connecting lug from damaging the tissue due to any sudden outward turns when the connecting lug is accidentally disengaged, or during release, pressing strips 423 corresponding to respective limiting grooves are further fixedly provided at the locking member 422. After the interventional instrument is loaded, the pressing strips 423 which are restrained by the sheath restrict the connecting lugs into the limiting grooves, to further improve the safety. During release, the pressing strips 423 of the flexible materials deflect outwardly to allow the connecting lug to be disengaged from the locking member 422.

The inner core 424 and the core tube 425 are both tubular. There is no relative movement required for the core tube 425 and the inner core 424 in the axial direction, so they may be nested, and welded at one or more welding points. If necessary, a bushing may be provided at the welding position to fill the radial gap between them. The inner core 424 and the core tube 425 are welded to the bushing respectively. The bushing may be made of the same material as the core tube 425.

One end of the core tube 425 is directly or indirectly fixed to the proximal end of the locking member 422, and the other end of the core tube 425 extends towards the operating handle.

In one embodiment, to facilitate the bending adjustment, the core tube 425 includes a compliant section 4251 adjacent to the locking member 422, and a third extension section 4252 connected end-to-end to the compliant section 4251 and extending proximally therefrom. The compliant section has less rigidity than the third extension section, that is, it has a better flexibility and can be more easily bent.

In one embodiment, the compliant section 4251 is a hypotube or a spring tube (that is, a spirally extending reinforcing rib provided in an interlayer of the tube wall). The length of the compliant section 4251 is in the range of 120 mm to 180 mm, for example, 150 mm.

The third extension section 4252 is a hypotube or a wire casing (which is woven or twisted with metal wires). The wire casing may be wrapped with a PTFE film which provides a lubricating function.

In other embodiments, the core tube 425 is entirely a hypotube. The hypotube can not only ensure the axial support but also be bent radially. To control the bending direction of the compliant section 4251, the compliant section 4251 can be provided with an axially extending reinforcing rib. The reinforcing rib is obtained by cutting a corresponding portion of the hypotube (where an uncut or less cut area is the reinforcing rib). The reinforcing rib may extend to the most proximal end of the core tube 425. However, since the core tube 425 has no obvious bending adjustment requirement at the position adjacent to the proximal end, the reinforcing rib can extend to the middle portion or a position just adjacent to the proximal end of the core tube 425.

Figure 7:
FIG. 7 is a schematic structural view of a core tube at the compliant section.
Figure 8:
FIG. 8 is a schematic structural view of another aspect of the core tube at the compliant section in FIG. 7.

Referring to FIGS. 7 and 8, when the compliant section 4251 is cut, the width of a cut slit (i.e. diameter of the laser spot) is 0.1 to 1 mm, and the slit spacing (i.e. the uncut portion left between adjacent two cutting slits) is 0.1 to 1 mm. An uncut portion extending along the axial direction serves as the reinforcing rib 4253.

In some embodiments, it is the core tube that is to be bent. The compliant section is configured such that, after being bent, the extreme radius of curvature is smaller closer to the distal end. This makes the distal end of the core tube more adaptable to complex paths. Specifically, for the compliant section, at least one of the following features may be present.

The slit width in the compliant section changes gradually, and it becomes increasingly larger as it approaches the distal end.

In the compliant section, the slit spacing gradually changes, and it becomes increasingly smaller as it approaches the distal end.

In the compliant section, the rigidity (flexibility) gradually changes, and the rigidity becomes increasingly smaller as it approaches the distal end.

Figure 9:
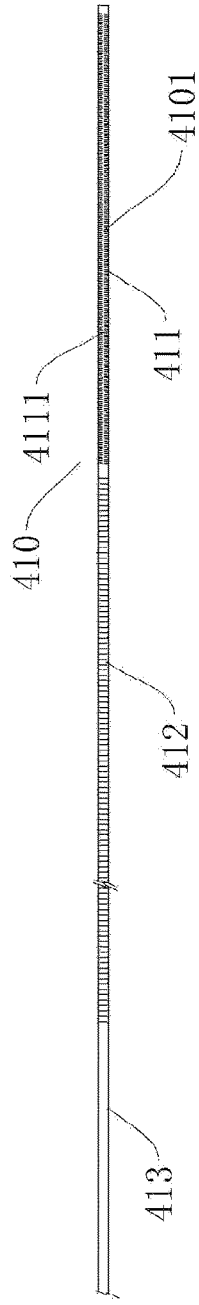
FIG. 9 is a schematic structural view of a bendable adjustable tube according to an embodiment of the present application.
Figure 10:
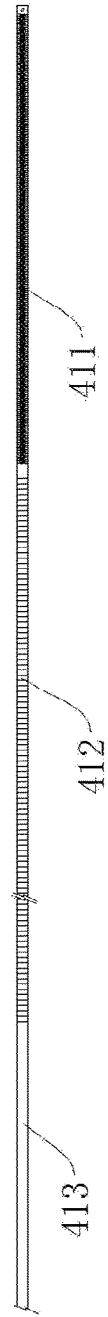
FIG. 10 is a schematic structural view of another aspect of the bendable adjustable tube in FIG. 9.
Figure 11:
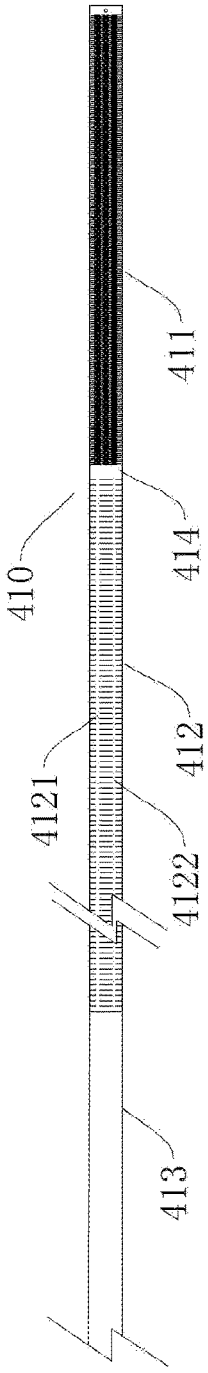
FIG. 11 shows the bendable adjustable tube in FIG. 9 after deployment.

Referring to FIGS. 9 to 11, the bendable adjustable tube 410 is mounted around the core tube 425, and the bendable adjustable tube 410 includes, in sequence from the distal end to the proximal end, a pulling section and a second extension section 413. The pulling section is in the form of a single piece, and it is a hypotube in this embodiment.

A distal end of the pulling section extends in proximity to the proximal end of the locking member 422 and is fixed to the core tube 425. To prevent the reverse positioning of the pulling section, a hole may be provided in the ends of the pulling section during processing to make different marks, to thereby identify the orientation of the distal and proximal ends during assembly.

The pulling section includes, in sequence from the distal end to the proximal end, a first pulling section 411, a transition section 414, and a second pulling section 412.

In this application, the bendable adjustable tube 410 is located outside the core tube 425, that is, the force applying element is arranged outside and the passively bent object is arranged inside during bending adjustment. Such an arrangement achieves a larger bending angle compared with an arrangement where the force applying element is arranged inside and the passively bent object is arranged outside.

The first pulling section 411 is provided with a reinforcing rib 4111 by cutting, which is offset from the reinforcing rib 4253 of the compliant section 4251 in the circumferential direction by 180 degrees.

The second pulling section 412 is also cut. When the first pulling section 411 and the second pulling section 412 are cut, the width of the cut slits are respectively 0.03 mm to 0.5 mm, and the slit spacings are 0.2 mm to 0.85 mm. The first pulling section 411 is located at an expected bending position, and is relatively softer and more flexible. The second pulling section 412 is relatively hard. However, to ensure that the second pulling section has a certain degree of flexibility to be bent during packaging and transportation, and be bent according to the blood vessel after entering the human body during the operation, the second pulling section is cut. In practice, the slit widths and slit spacings in different sections can be adjusted according to the actual rigidity requirements.

The second pulling section 412 is cut to form reinforcing ribs 4121 and 4122. The two reinforcing ribs are radially opposite to each other. That is, the two reinforcing ribs are circumferentially offset by 180 degrees. The two reinforcing ribs are both circumferentially offset from the reinforcing rib 4111 of the first pulling section 411 by 90 degrees.

The transition section 414 is not cut. The transition section 414 connects the first pulling section 411 to the second pulling section 412, and bears the stress at different positions in the circumferential direction.

There is no particular bending requirement for the second extension section 413. It mainly serves to transmit the pulling force. For example, an uncut hypotube may be used, which extends proximally and is connected to the operating handle.

During the bending adjustment process, the first pulling section 411 and the compliant section 4251 are mainly bent to a greater degree. Therefore, when a hypotube is cut, a target bending angle greater than 270° is generally required. The first pulling section and the compliant section are respectively provided with a single reinforcing rib structure, which ensures that no stretch occurs during the bending adjustment. The first pulling section 411 and the compliant section 4251 which are aligned in the radial direction have a moderate flexibility, facilitating the bending adjustment while ensuring the force transmission. In general, the bendable adjustable tube 410 is 5 to 10 mm longer than the core tube 425, to compensate for axial offset after bending. The core tube 425 and the sheath 300 are passive elements during the bending adjustment, and the bendable adjustable tube 410 is the force applying element.

Figure 12:
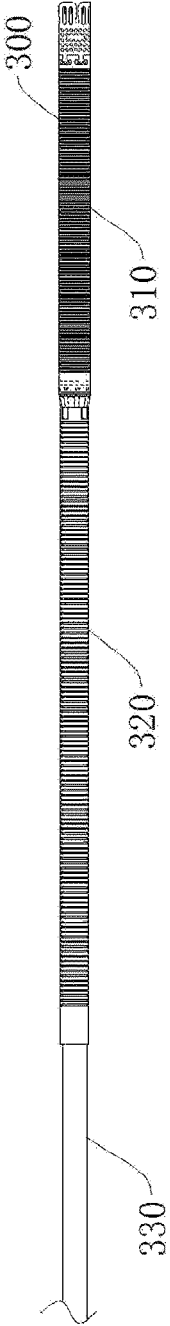
FIG. 12 is a schematic structural view of a sheath according to an embodiment of the present application.
Figure 13:
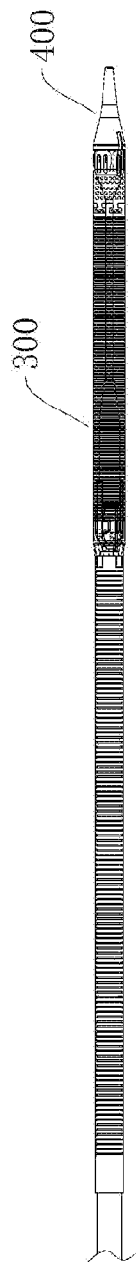
FIG. 13 is a schematic view showing the structure obtained after the components in FIG. 5c, FIG. 6, and FIG. 12 are assembled.

Referring to FIGS. 12 to 13, in order to adapt to the bending adjustment or adjust the orientation of the distal end adaptively when traveling in the body, the outermost sheath 300 has different flexibilities at different axial sections. The sheath 300 includes, from the distal end to the proximal end, a loading section 310, a bendable section 320, and a first extension section 330. During use, the bend mainly occurs at a position adjacent to the proximal end of the loading section which is configured for accommodating the interventional instrument 500, i.e., at the bendable section 320.

Figure 14:
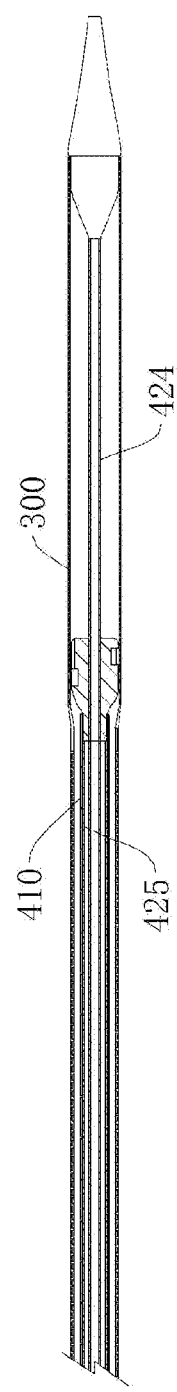
FIG. 14 is a cross-sectional view of a sheath assembly according to an embodiment of the present application.
Figure 15A:
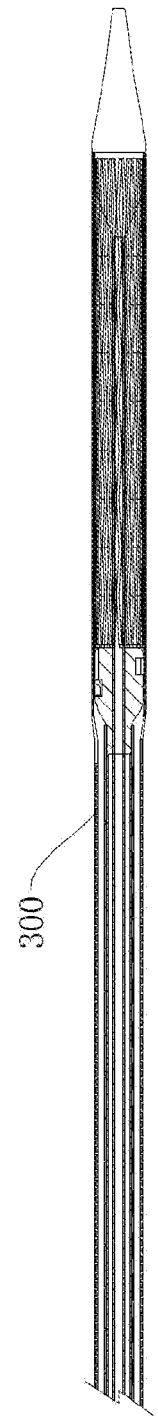
FIG. 15a is a schematic structural view of the sheath assembly in FIG. 14 with an interventional instrument loaded therein.
Figure 15B:
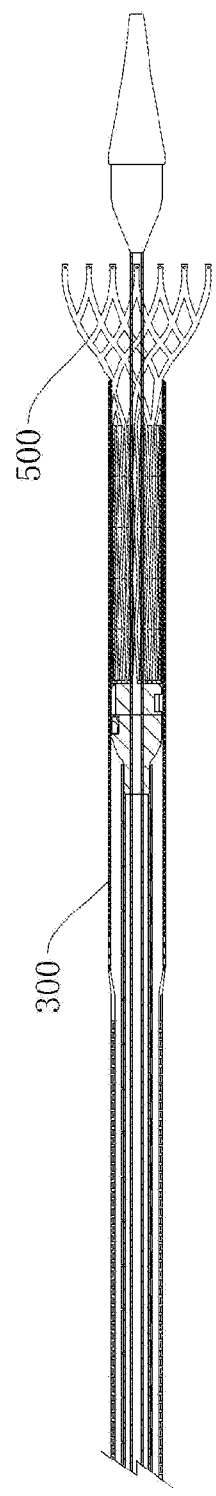
FIG. 15b is a schematic structural view showing the interventional instrument in FIG. 15a partially released.

Referring to FIGS. 14 to 15d, according to one embodiment, the nesting relationship of the sheath 300, the core tube component 420, and the bendable adjustable tube 410, and the release process of the interventional instrument, are illustrated. FIG. 15d also illustrates the approximate axial positional relationships of various sections of the sheath 300, the core tube component 420, and the bendable adjustable tube 410. The sheath 300 has a multi-layer composite structure in each section. Specifically, for a certain section, a multi-layer structure is adopted which includes different parts during processing. The structure and the manufacturing process of the sheath 300 are also the improvements of this application.

Figure 17A:
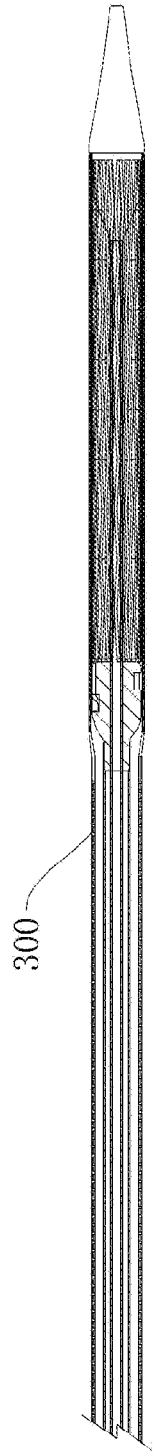
FIG. 17a is a schematic structural view of the structure in FIG. 16, wherein an interventional instrument is loaded.
Figure 17B:
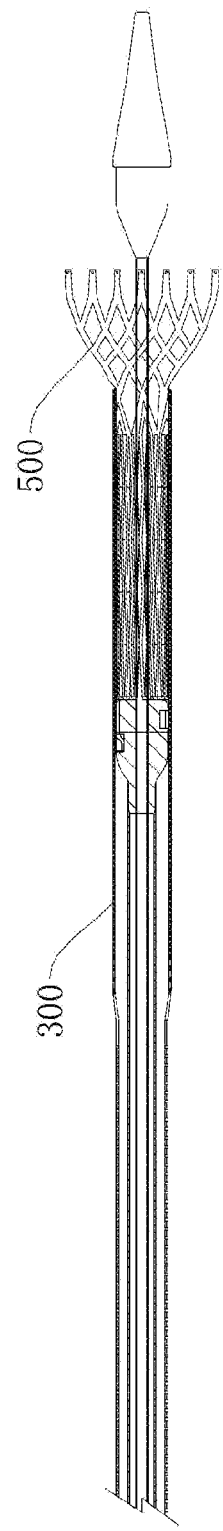
FIG. 17b is a schematic structural view showing the interventional instrument in FIG. 17a half-released.
Figure 17C:
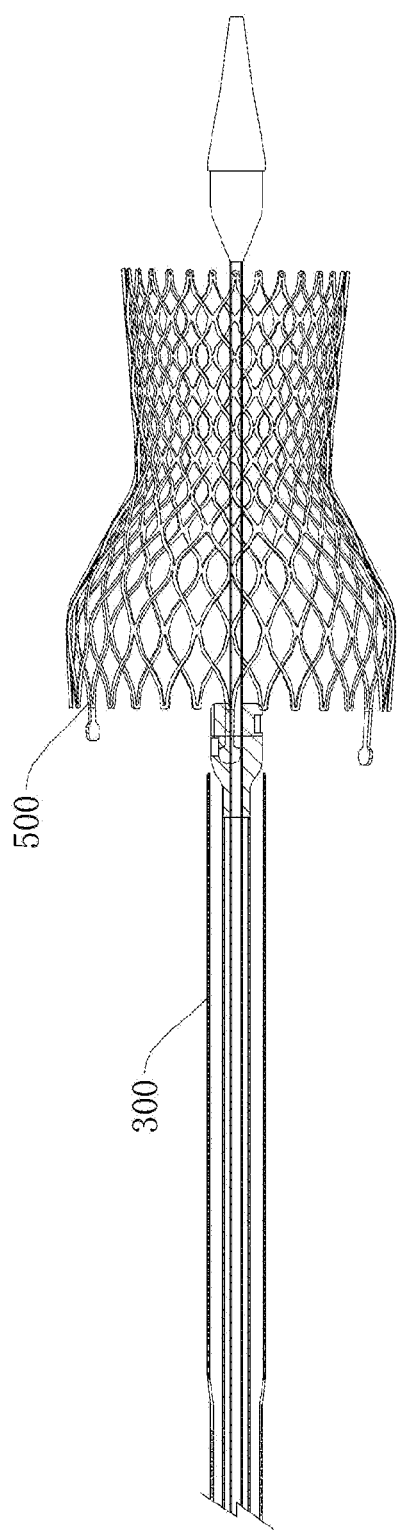
FIG. 17c is a schematic structural view showing the interventional instrument in FIG. 17a completely released.
Figure 18:
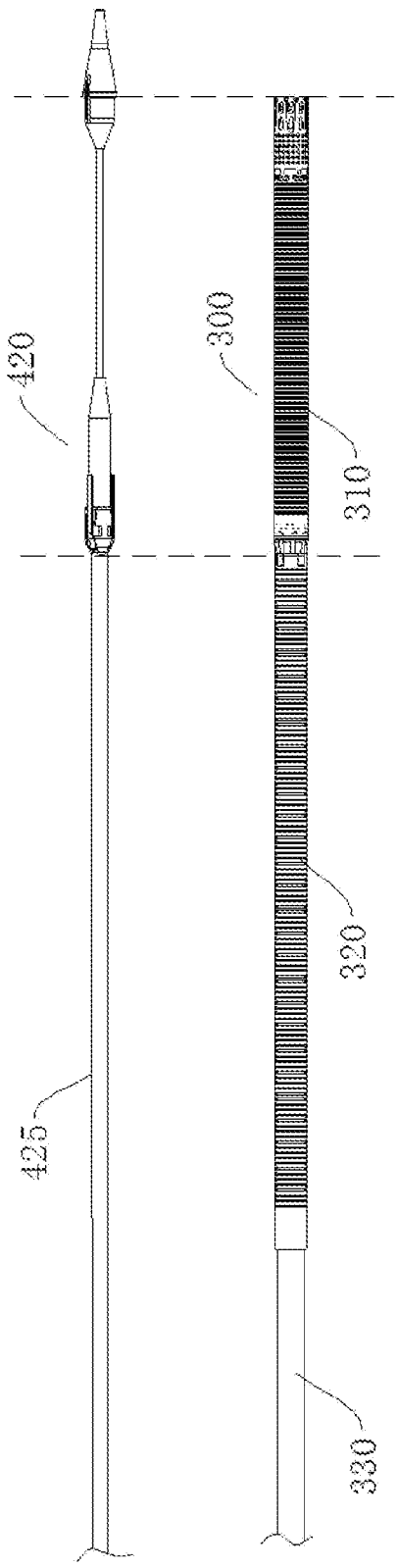
FIG. 18 is a schematic view showing the relative relationships between the axial sections of each tube according to an embodiment of the present application.

Referring to FIGS. 16 to 18, according to one embodiment, the nesting relationship of the sheath 300 and the core tube component 420, and the release process of the interventional instrument (in which a bendable adjustable tube 410 is not provided compared with the above embodiments), are illustrated. FIG. 15d also illustrates the approximate axial positional relationships of various sections of the sheath 300 and the core tube component 420. The sheath 300 has a multi-layer composite structure in each section. That is, for a certain section, a multi-layer structure is adopted which includes different parts during processing. The structure of the sheath 300 and the manufacturing process are also one of the improvements of this application. In this embodiment, the core tube component 420 includes the core tube 425. The locking member 422 is fixed on the core tube 425. The distal end of the core tube 425 further extends out of the locking member 422, and the guide head 421 is fixed at the most distal end. A distal end of the guide head 421 has a conical-shaped head structure to facilitate travel in the human body. A position between the guide head 421 and the locking member 422 is configured as the loading position for the interventional instrument. The compressed interventional instrument is located at this position, fitted to and restrained by the locking member 422.

In one embodiment, the core tube 425 is provided therein with the inner core 424 extending therethrough. The distal end of the inner core 424 extends out of the locking member 422 and is fixed to the guide head 421. The distal end of the core tube 425 extends just to the locking member 422. The extension length of the proximal end of the inner core 424 is not strictly limited. Since the core tube 425 does not extend to the loading position, and the inner core 424 has a smaller outer diameter compared with the core tube 425, the radial space of the loading position can be increased.

An embodiment of the present application provides a sheath for delivering an interventional instrument. A distal end of the sheath is the loading section 310 configured for accommodating the interventional instrument. The loading section 310 has a multi-layer structure and includes, from an inner side to an outer side, an inner lining tube, a metal tube, and an outer wrapping membrane 380. The metal tube includes, from a proximal end to a distal end, a main tube 350 and a head tube 340. The head tube 340 may use the distal end structure of a sheath according to the various embodiments shown in FIGS. 1a to 1d.

The main tube 350 and the head tube 340 may be formed as one piece by cutting, or separate pieces connected end-to-end.

In case that they are separate pieces, for example, the proximal end of the body section in the head tube 340 has a first connector 343, and the distal end of the main tube 350 has a second connector 351. The first connector 343 and the second connector 351 are fitted with each other through form-fitting. It is also possible that they are inserted and nesting in each other.

Another embodiment of the present application provides a sheath for delivering an interventional instrument. The sheath includes, in sequence from the proximal end to the distal end, the loading section 310, the bendable section 320, and the first extension section 330 in an axial direction. The loading section 310 is configured for accommodating an interventional instrument 500. The sheath has a multi-layer structure and includes:

an inner sheath 370, distributed in the bendable section and the first extension section in the axial direction;

an inner lining tube, connected end-to-end to a distal end of the inner sheath 370, and distributed in the loading section in the axial direction;

a metal tube, surrounding the outer peripheries of the distal portion of the inner sheath and the inner lining tube, and distributed in the bendable section and the loading section in the axial direction, the metal tube includes, in sequence from a distal end to a proximal end, the head tube 340, the main tube 350, and an extension tube 360, wherein in the axial direction, the head tube and the main tube are both distributed in the loading section, and the extension tube is distributed in the bendable section; and the head tube 340 may use a distal end structure of a sheath for delivering an interventional instrument according to various embodiments as shown in FIGS. a-1d; and an outer wrapping membrane 380, wrapped around the outer periphery of the metal tube, and distributed in the bendable section and the loading section in the axial direction.

Figure 19:
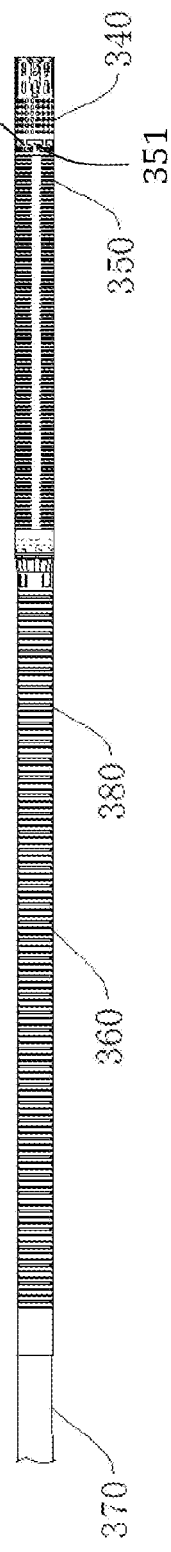
FIG. 19 is a schematic view showing each component in a sheath.
Figure 20:
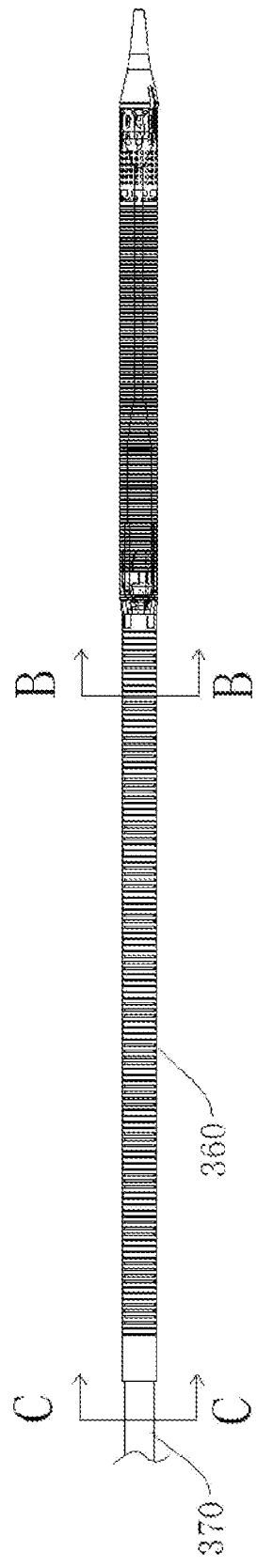
FIG. 20 is a schematic view of a distal end portion of a delivery system according to the present application.
Figure 21:
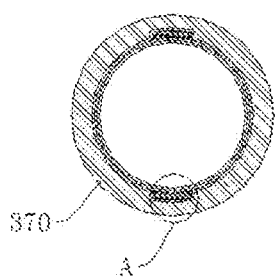
FIG. 21 is a cross-sectional view of an inner sheath in FIG. 20 at position C-C.
Figure 22:
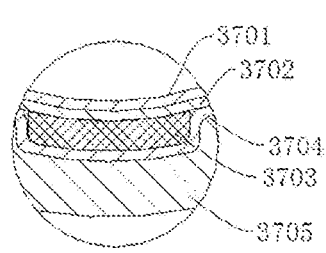
FIG. 22 is an enlarged view of area A in FIG. 21.
Figure 23:
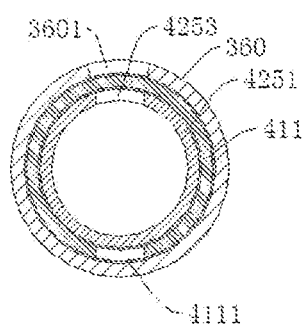
FIG. 23 is a cross-sectional view of FIG. 20 at position B-B.
Figure 24:
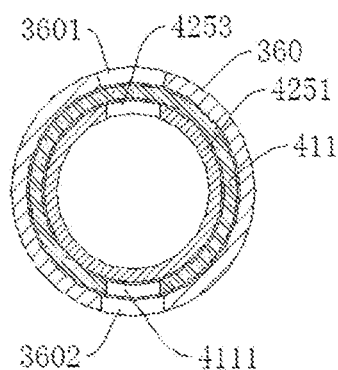
FIG. 24 is a cross-sectional view of FIG. 20 at position B-B according to another embodiment.

The loading section 310 needs to surround the interventional instrument, and thus the loading section 310 has a larger diameter than the portions of the sheath at a proximal end of the loading section 310, i.e., the bendable section 320 and the first extension section 330. FIG. 19 shows a portion of visible parts of the sheath 300. The distal portion of the sheath 300 has at least three layers in general. The inner and outer layers are made of polymer materials, and the middle layer is a metal tube.

The bendable section can be bent to change the orientation of the distal end of the sheath during delivery. The first extension section mainly serves to provide sufficient axial pushing force and pulling force, and has a sufficient length to connect to the operating handle.

The head tube 340 is formed by cutting a nickel-titanium alloy tube. The main tube 350 and the extension tube 360 are each formed by cutting a stainless steel tube. The head tube 340 and the main tube 350 have larger diameters than the extension tube 360 as they need to enclose the interventional instrument. Referring to the axial positional relationship shown in FIG. 19, it can be seen that the joint portion of the main tube 350 and the extension tube 360 is flared accordingly and has a diameter that increases gradually.

To prevent the metal material of the intermediate layer from scratching the inner wall of the blood vessel, the outermost layer wraps the head tube 340, the main tube 350 and the extension tube 360. The outer wrapping membrane 380 of the outermost layer can be made of a polymer material. Since the metal portion has multiple sections, the outer wrapping membrane 380 also has multiple sections which are connected one another and melted together during processing.

For example, along the axial direction of the sheath, the outer wrapping membrane 380 includes multiple sections, and the sections are made of different materials, or at least two of them are made of a same material.

In one embodiment, the strength of the outer wrapping membrane corresponding to the main tube 350 is greater than the strength of the outer wrapping membrane corresponding to the distal end of the head tube 340.

The inner layer includes the inner sheath 370 and the inner lining tube. One end of the inner sheath 370 extends proximally, and the other end extends to the joint portion of the main tube 350 and the extension tube 360. The inner lining tube further extends distally from the joint portion of the main tube 350 and the extension tube 360 to reach the distal side of the head tube 340, wherein the inner lining tube can be made of PTFE.

The axial position of the distal portion of the extension tube 360 corresponds to the compliant section 4251 and the first pulling section 411, and the extension tube 360 can also form a reinforcing rib by cutting.

Referring to FIGS. 20 to 24, the inner sheath 370 has a multi-layer structure, and includes, from the inside to the outside, an inner layer 3701 of PTFE, a woven layer 3702, a woven layer 3704, and an outer layer 3705. Two reinforcing ribs 3703 extending in the axial direction are fixedly sandwiched between the woven layer 3702 and the woven layer 3704.

One of the two reinforcing ribs 3703 is located at the same circumferential position as the reinforcing rib 4253, and the circumferential position of the other reinforcing rib 3704 is offset from that of the reinforcing rib 4253 by 180 degrees.

The woven layer 3702 and the woven layer 3704 are not required to have an obvious contour, and may be woven as one piece with the reinforcing ribs sandwiched therein. The outer layer 3705 may be made of Pebax.

The reinforcing rib 4253 provided in the compliant section 4251 and the reinforcing rib 4111 provided in the first pulling section 411 are circumferentially offset by 180 degrees.

The cross-sectional view only shows the extension tube 360 of the sheath. The extension tube 360 may be provided with a reinforcing rib 3601, which is radially aligned with the reinforcing rib 4253, that is, the reinforcing rib 3601 and the reinforcing rib 4253 are located at the same circumferential position.

In another embodiment, the extension tube 360 may be provided with two reinforcing ribs, namely a reinforcing rib 3601 and a reinforcing rib 3602. The reinforcing rib 3601 is radially aligned with the reinforcing rib 4253, that is, they are located at the same circumferential position. The reinforcing rib 3602 is aligned with the reinforcing rib 4111, that is, they are located at the same circumferential position which is offset from that of the reinforcing rib 4253 by 180 degrees.

The inner sheath 370 exists not only in the bendable section 320 but also in the first extension section 330. As the bendable section 320 has a larger bending angle during bending adjustment, the inner sheath 370 has different strengths in the bendable section 320 and in the first extension section 330. The inner sheath 370 is softer in the bendable section 320. For example, the outer layer 3705 of the inner sheath 370 at the bendable section 320 is made of Pebax of 30-59D, and the outer layer 3705 of the inner sheath 370 at the first extension section 330 is made of Pebax of 60-90D. The woven layer and the PTFE inner layer 3701 of the inner sheath 370 at different sections can have the same configurations.

Figure 25:
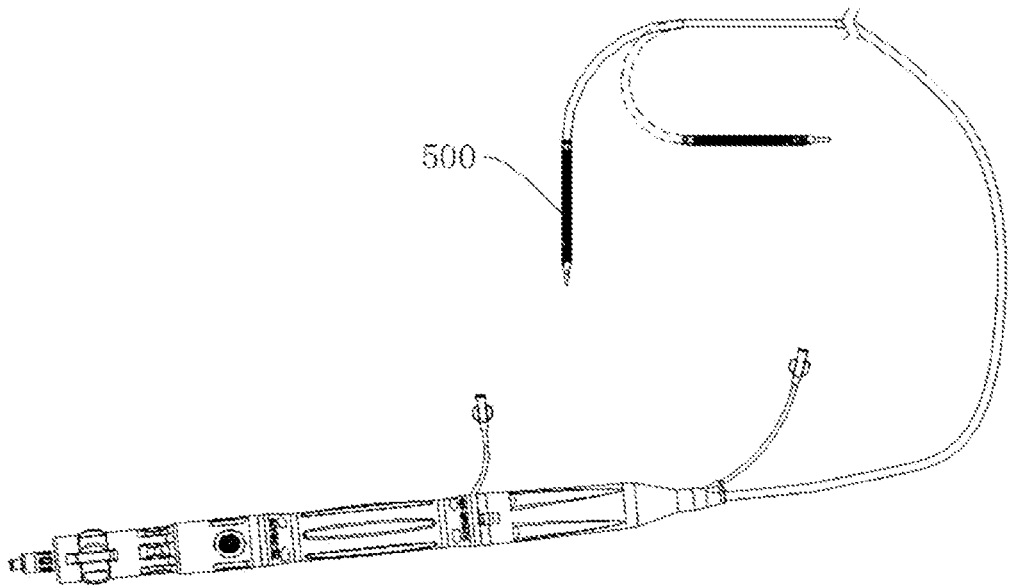
FIG. 25 is a schematic view showing the change of a distal end during the bending adjustment of an interventional instrument delivery system according to the present application.

Referring to FIG. 25, during use, the bending adjustment system of the present application is able to actively change the orientation of the distal portion by pulling the bendable adjustable tube with the operating handle, thus facilitating the delivery of an interventional instrument 500 within a complex path. Because it is the core tube component that is pulled by the bendable adjustable tube, when the interventional instrument is released by withdrawing the sheath, the orientation of the interventional instrument loaded on the core tube component is kept unchanged, thus avoiding a potential risk of incorrect positioning during the release process.

The features described in the above various embodiments may be combined. In order to simplify the descriptions, not all possible combinations of the features in the above embodiments have been described. However, any combinations of the features should be within the scope of the disclosure as long as no conflict resides between these features. In the case where the features in different embodiments are shown in the same drawing, it may be considered that this drawing discloses a combination of the various embodiments involved.

The above embodiments are only several implementations of the present application, which are described specifically and in detail, without limitation to the scope claimed by the present application. It should be noted that those skilled in the art can make various modifications and variations to the embodiments without departing from the spirit and scope of the present application, and these modifications and variations should fall into the scope claimed by the present application.

What is claimed is:

1. A sheath for delivering an interventional instrument, comprising, from a distal end to a proximal end, a loading section, a bendable section, and a first extension section in an axial direction, wherein the sheath has a multi-layer structure, comprising:
    an inner sheath, distributed in the bendable section and the first extension section in the axial direction;
    an inner lining tube, connected end-to-end to a distal end of the inner sheath, and distributed in the loading section in the axial direction;
    a metal tube, surrounding a distal portion of the inner sheath and an outer periphery of the inner lining tube, and comprising, from a distal end to a proximal end, a head tube, a main tube, and an extension tube arranged in sequence, wherein in the axial direction, the head tube and the main tube are both distributed in the loading section, and the extension tube is distributed in the bendable section; and wherein the head tube has a distal end structure; and
    an outer wrapping membrane, wrapped around an outer periphery of the metal tube, and distributed in the bendable section and the loading section in the axial direction,
    wherein the distal end structure comprises a tubular body section, the body section has opposite distal and proximal sides, a plurality of elastic expansion pieces are arranged circumferentially at the distal side of the body section at intervals, each expansion piece assumes a converged configuration extending in an axial direction of the body section and a flared configuration away from each other, wherein a connecting strip is provided between two adjacent expansion pieces, and two ends of the connecting strip are respectively connected to expansion pieces at respective sides at connection positions adjacent to distal ends of the expansion pieces, wherein
    in the converged configuration of each expansion piece, a middle portion of the connecting strip is folded and received in a region between two adjacent expansion pieces;
    in the flared configuration of each expansion piece, the middle portion of the connecting strip is unfolded; and
    wherein in the converged configuration of each expansion piece, the middle portion of the connecting strip is U-shaped at a proximal side, a bottom of the U-shaped structure has two corner portions, and an outside of each corner portion is provided with a protrusion.

2. A sheath for delivering an interventional instrument, comprising a distal end as a loading section for accommodating the interventional instrument, wherein the loading section has a multi-layer structure and comprises from inside to outside, an inner lining tube, a metal tube and an outer wrapping membrane, wherein a plurality of elastic expansion pieces are arranged circumferentially at a distal side of the metal tube at intervals, each expansion piece assumes a converged configuration extending in an axial direction of the metal tube and a flared configuration away from each other, wherein a plurality of connecting strips are provided, each connecting strip is provided between two adjacent expansion pieces, and two ends of each connecting strip are respectively connected to expansion pieces at respective sides at connection positions adjacent to distal ends of the expansion pieces, wherein
    in the converged configuration of each expansion piece, a middle portion of each connecting strip is folded and received in a region between two adjacent expansion pieces;
    in the flared configuration of each expansion piece, the middle portion of each connecting strip is unfolded; and
    wherein in the converged configuration of each expansion piece, the middle portion of each connecting strip is U-shaped at a proximal side, a bottom of the U-shaped structure has two corner portions, and an outside of each corner portion is provided with a protrusion.

3. The sheath for delivering an interventional instrument according to claim 2, wherein the metal tube comprises, from a proximal end to a distal end, a main tube and a head tube; and the head tube has a distal end structure, wherein the distal end structure comprises a tubular body section, the body section has opposite distal and proximal sides.

4. The sheath for delivering an interventional instrument according to claim 3, wherein the main tube and the head tube are formed as one piece by cutting, or as separate pieces that are connected end-to-end.

5. The sheath for delivering an interventional instrument according to claim 3, wherein all the connecting strips extend continuously in a circumferential direction of the body section.

6. The sheath for delivering an interventional instrument according to claim 3, wherein the body section, the expansion pieces and the connecting strips are formed as one piece.

7. The sheath for delivering an interventional instrument according to claim 3, wherein the distal end structure of the head tube is formed by cutting a tube having a shape memory property.

8. The sheath for delivering an interventional instrument according to claim 3, wherein a plurality of hollow areas are provided on a side wall of the body section, and the proximal side of the body section has a connector that fits to other part of the sheath.

9. The sheath for delivering an interventional instrument according to claim 8, wherein the hollow areas are a plurality of through holes, and the through holes on the body section are randomly arranged or arranged in an array on a peripheral surface.

10. The sheath for delivering an interventional instrument according to claim 2, wherein a distal lateral edge of each expansion piece has an arc shape, and each connecting strip extends substantially along a tangential direction of the arc and is then connected to the distal lateral edge of a respective expansion piece.

11. The sheath for delivering an interventional instrument according to claim 10, wherein two adjacent connecting strips are connected end-to-end at the distal lateral edge of the same expansion piece, and the distal lateral edge at the connection position is smoothly transitioned.

12. The sheath for delivering an interventional instrument according to claim 2, wherein in the flared configuration of each expansion piece, the two protrusions of the same U-shaped structure are adjacent to or abut against each other.

13. The sheath for delivering an interventional instrument according to claim 2, wherein an opening is provided between two adjacent expansion pieces; and in the converged configuration of each expansion piece, a corresponding connecting strip extends into the opening along an arc-shaped path from its two ends.

14. The sheath for delivering an interventional instrument according to claim 13, wherein in the converged configuration of each expansion piece, a proximal side of the corresponding connecting strip is in proximity of a middle portion of the opening in the axial direction of the metal tube.

15. The sheath for delivering an interventional instrument according to claim 13, wherein in the axial direction of the metal tube, the opening is widened in the middle portion and narrowed at two ends.

16. The sheath for delivering an interventional instrument according to claim 2, wherein in the flared configuration of each expansion piece, each connecting strip has a V-shape, and an apex angle of the V-shape is greater than or equal to 120 degrees.

17. The sheath for delivering an interventional instrument according to claim 2, wherein each expansion piece has at least one hollow area, and the expansion pieces are arranged circumferentially, and the number of the expansion pieces ranges from 3 to 6.

18. The sheath for delivering an interventional instrument according to claim 17, wherein the total area of the at least one hollow area on the same expansion piece is less than 50% of the area of the same expansion piece.

19. The sheath for delivering an interventional instrument according to claim 18, wherein the at least one hollow area comprises a plurality of through holes, and the through holes on the same expansion piece are arranged on the sheath axially or circumferentially in intervals.

* * * * *